US010632476B2

(12) United States Patent
Meisberger et al.

(10) Patent No.: US 10,632,476 B2
(45) Date of Patent: Apr. 28, 2020

(54) METHOD FOR PROCESSING A LIQUID MEDIUM COMPRISING CELLS

(71) Applicant: Fresenius Kabi Deutschland GmbH, Bad Homburg (DE)

(72) Inventors: Artur Meisberger, St. Wendel (DE); Melanie Fahrendorff, Niederkassel (DE); Michael Brinkmann, Niddatal (DE); Martin Biehl, St. Wendel (DE)

(73) Assignee: Fresenius Kabi Deutschland GmbH, Bod Homberg (DE)

( * ) Notice: Subject to any disclaimer, the term of this patent is extended or adjusted under 35 U.S.C. 154(b) by 0 days.

(21) Appl. No.: 16/028,636

(22) Filed: Jul. 6, 2018

(65) Prior Publication Data
US 2018/0333419 A1 Nov. 22, 2018

Related U.S. Application Data

(62) Division of application No. 15/035,711, filed as application No. PCT/EP2014/078121 on Dec. 17, 2014, now Pat. No. 10,022,732.

(30) Foreign Application Priority Data

Jan. 27, 2014 (EP) .................................. 14152634

(51) Int. Cl.
*B04B 9/10* (2006.01)
*A61M 1/02* (2006.01)
(Continued)

(52) U.S. Cl.
CPC ............. *B04B 9/10* (2013.01); *A61M 1/0272* (2013.01); *A61M 1/3692* (2014.02);
(Continued)

(58) Field of Classification Search
CPC ......... B04B 11/02; B04B 5/0442; B04B 9/10; A61M 1/0272; A61M 1/3692; A61M 1/3696
See application file for complete search history.

(56) References Cited

U.S. PATENT DOCUMENTS 4,935,002 A 6/1990 Gordon
4,943,273 A 7/1990 Pages
(Continued)

FOREIGN PATENT DOCUMENTS

CN 1322146 11/2001
CN 101172207 5/2008
(Continued)

OTHER PUBLICATIONS

Dai et al., Continuous and Discontinuous Cell-Washing Autotransfusion Systems, J. Cardiothoracic and Vascular Anesthesia, vol. 18, No. 2, pp. 210-217 (Apr. 2004).
(Continued)

*Primary Examiner* — Timothy C Cleveland
(74) *Attorney, Agent, or Firm* — Cook Alex Ltd.

(57) ABSTRACT

A method for processing an initial liquid medium including cells in an initial concentration to obtain a product liquid medium including cells in a product concentration includes supplying the initial medium to a separator via a first supply system, separating the initial medium into various constituents including the product medium, extracting the product medium from the separator via a first outlet system, measuring a physical parameter related to the concentration of the cells in the initial medium using a sensor, and controlling at least one process parameter as a function of the physical parameter. During the step of separating the initial medium, a solution is supplied to the separator at a flow rate via a second supply system. The flow rate of the solution is determined based on the at least one process parameter, and
(Continued)

is reduced when the concentration of the cells measured in the initial medium increases.

12 Claims, 3 Drawing Sheets

(51) Int. Cl.
- *A61M 1/36* (2006.01)
- *B04B 5/04* (2006.01)
- *B04B 11/02* (2006.01)

(52) U.S. Cl.
CPC ......... *A61M 1/3696* (2014.02); *B04B 5/0442* (2013.01); *B04B 11/02* (2013.01)

(56) References Cited

U.S. PATENT DOCUMENTS

| | | | |
|---|---|---|---|
| 5,298,171 | A | 3/1994 | Biesel |
| 6,284,142 | B1 | 9/2001 | Muller |
| 6,299,784 | B1 | 10/2001 | Biesel |
| 7,479,123 | B2 | 1/2009 | Briggs |
| 7,833,185 | B2 | 11/2010 | Felt et al. |
| 2003/0222029 | A1 | 12/2003 | Muller |
| 2013/0310241 | A1 | 11/2013 | Kabaha et al. |

FOREIGN PATENT DOCUMENTS

| | | |
|---|---|---|
| EP | 0 528 238 B1 | 2/1993 |
| EP | 0 682 953 A1 | 11/1995 |
| EP | 0 527 973 B1 | 4/1998 |
| EP | 0 799 645 31 | 3/2002 |
| EP | 1 925 327 31 | 5/2008 |
| JP | H11-267195 | 10/1999 |
| JP | 2000-217908 | 8/2000 |
| JP | 2005-103256 | 4/2005 |
| JP | 2008-525107 | 7/2008 |
| JP | 2008-194067 | 8/2008 |
| WO | WO 90/00069 | 1/1990 |

OTHER PUBLICATIONS

International Search Report and Written Opinion, counterpart International Appl. No. PCT/EP2014/078121 (dated Mar. 5, 2015).

Shulman, Quality of Processed Blood for Autotransfusion, J. Extra-Corporeal Tech., vol. 32, No. 1, pp. 11-19 (Mar. 2000).

Strasser et al., CD14+cell collection in non-cytokine-stimulated donors with the COM.TEC cell separator, Transfusion, vol. 46, pp. 66-73 (Jan. 2006).

Walpoth et al., Qualitative assessment of blood washing with the continuous autologous transfusion system, Int'l J. Artificial Organs, vol. 20, No. 4, pp. 234-239 (1997).

Zeiler et al,, Platelet Concentrates from Automated Apheresis—Past, Present and Future Developments, Infusion Therapy Transfusion Medicine, pp. 119-126 (Mar. 2000).

METHOD FOR PROCESSING A LIQUID MEDIUM COMPRISING CELLS

The present application is a divisional of U.S. application Ser. No. 15/035,711, which is a U.S. National Stage of PCT International Patent Application No. PCT/EP2014/078121, filed Dec. 17, 2014, which claims priority to EP Application No. 14 152 634.3, filed Jan. 27, 2014, all of which are hereby incorporated herein by reference in their entirety.

TECHNICAL FIELD

The invention relates to a device and method for processing an initial liquid medium comprising cells in an initial concentration to obtain a product liquid medium comprising cells in a product concentration. The cells may be living cells.

BACKGROUND

Devices for processing an initial liquid medium comprising cells in an initial concentration to obtain a product liquid medium comprising cells in a product concentration and corresponding methods are known. The devices typically comprise a separator adapted to separate the initial liquid medium into various constituents, a first supply system for supplying the initial liquid medium to the separator, a first outlet system for extracting the product liquid medium from the separator, a sensor adapted to measure a physical parameter related to the concentration of the cells in the initial or product liquid medium, and a control unit coupled to the sensor and adapted to control at least one process parameter of the device as a function of the physical parameter measured by the sensor.

Such devices are typically used for separating blood into various constituents, in particular for extracting red blood cells (erythrocytes) as described for example in EP 0 528 238 B1. The known device for the separation of blood into various constituents is adapted for in-vivo-processing, in particular for intraoperative blood processing and comprises a separator which has one intake line with a pump and a discharge line for the erythrocyte fraction. To control the pump of the intake line, a sensor for a continuous measurement of the hematocrit value is provided in the intake line. The measured hematocrit value serves as an input for regulating means. The output of that regulating means is used to adjust the blood flow through the pump depending on the measured hematocrit signal.

It is an object of the present invention to improve such device such that it can be used for in vivo and in vitro processing of an initial liquid medium comprising cells in an initial concentration to obtain a product liquid medium comprising cells in a product concentration.

SUMMARY

According to an aspect, a method for processing an initial liquid medium including cells in an initial concentration in order to obtain a product liquid medium including cells in a product concentration is provided. The method includes supplying the initial liquid medium to a separator via a first supply system, in the separator, separating the initial liquid medium into various constituents including the product liquid medium, extracting the product liquid medium from the separator via a first outlet system, measuring a physical parameter related to the concentration of the cells in the initial liquid medium using a sensor, and controlling at least one process parameter as a function of the physical parameter measured by the sensor. During the step of separating the initial liquid medium into various constituents, a solution is supplied to the separator at a flow rate via a second supply system. The flow rate of the solution in the second supply system during its supply to the separator is determined based on the at least one process parameter, and the flow rate of the solution in the second supply system is reduced when the concentration of the cells measured in the initial liquid medium increases.

The solution supplied via the second supply system may be used for processing the initial liquid medium and washed out to obtain the product liquid medium. For example, the solution may be a washing solution, such as a physiologic saline solution, a cell culture medium, plasma, albumin or the like. The flow rate of the solution in the second supply system during its supply to the separator is determined based on the at least one process parameter, which at least one process parameter may be of the device that is controlled by a control unit coupled to the sensor. In particular, the control unit can be configured such that it reduces the flow rate of the solution in the second supply system if the concentration of the cells measured in the initial liquid medium increases. While in vivo processing requires substantially the same flow rate of the solution in the second supply system, this flow rate for in vitro processing may vary depending on the processing speed or the quality of the product liquid medium desired. In particular, the possibility to vary the flow rate of the second supply system enables the device to operate in vitro.

In addition to determining the flow rate of the solution in the second supply system, the process parameter, which may be controlled by the control unit, can also determine the flow rate of the initial liquid medium in the first supply system during its supply to the separator and/or the flow rate of the product liquid medium in the first outlet system during its extraction from the separator. The flow rate of the initial liquid medium can be controlled (e.g., by the control unit) to be indirectly proportional to the initial concentration of the cells in the initial liquid medium in the first supply system. The flow rate of the product liquid medium can also be controlled to be directly proportional to the initial concentration of the cells in the initial liquid medium in the first supply system.

According to one aspect of the invention, the separator is a centrifuge that is adapted to separate the initial liquid medium into various constituents. The centrifuge can be designed as a planar spiral channel. Alternatively, the centrifuge may be a bell shaped bowl. The process parameter may be used to control the rotational speed of the centrifuge. Preferably, the rotational speed may be controlled to be indirectly proportional to the initial concentration of the cells in the initial liquid medium in the first supply system. The separator can operate continuously or discontinuously (batch-wise).

Alternatively, the separator can be a membrane, such as a spinning membrane, a flat sheet membrane or a hollow fiber membrane.

The first supply system may include a supply line through which the initial liquid medium flows into the separator. Correspondingly, the first outlet system may include an output line through which the product liquid medium flows out of the separator. In case that the sensor measures a physical parameter related to the initial concentration of the cells in the initial liquid medium, the measurement is preferably performed for the initial liquid medium that is present in the supply line of the first supply system. In case that the sensor measures a physical parameter related to the product concentration of the cells in the product liquid medium, the measurement is preferably performed for the product liquid medium that is present in the output line of the first outlet system.

To obtain a product liquid medium of essentially constant quality with respect to the concentration of cells, the at least one process parameter of the device may be controlled such that the product concentration of the cells in the product liquid medium is within a predefined range of concentration. Alternatively, the at least one process parameter of the device may be controlled to maximize the product concentration of the cells in the product liquid medium.

According to another embodiment, the device comprises two sensors, a first sensor being adapted to measure a physical parameter related to the concentration of the cells in the initial liquid medium and a second sensor adapted to measure a physical parameter related to the concentration of the cells in the product liquid medium.

DESCRIPTION OF THE DRAWINGS

The idea underlying the invention shall subsequently be described in more detail with reference to the embodiments shown in the figures. Herein.

DETAILED DESCRIPTION

Figure 1:
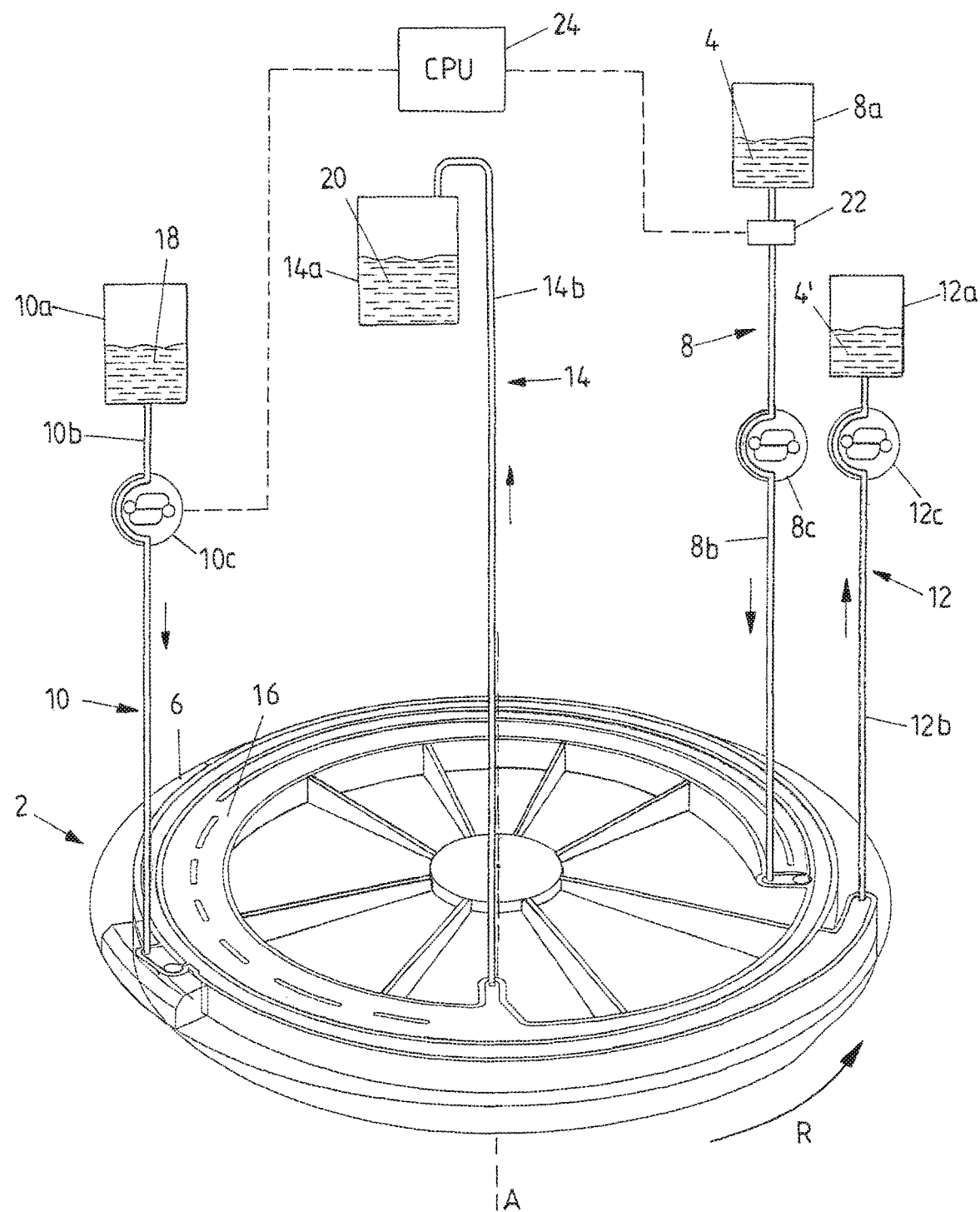
FIG. 1 shows a schematic view of a device for processing a liquid medium comprising cells according to a first embodiment of the invention.

FIG. 1 shows a first embodiment of a device 2 for processing an initial liquid medium 4 comprising cells in an initial concentration to obtain a product liquid medium 4' comprising cells in a product concentration. The product concentration is intended to be higher than the initial concentration. As an example, said initial liquid medium 4 can be blood comprising blood cells (mainly red blood cells, but also white blood cells and platelets) and plasma. Here, the cells of interest shall be the red blood cells, also referred to as erythrocytes. The volume percentage of red blood cells in blood is referred to as hematocrit. The product liquid medium 4' shall be the erythrocyte fraction separated from the blood. Furthermore, the initial liquid medium 4 can comprise major proportions of rinsing solution, fat, debris and/or particular components such as tissue, small bone particles or the like. These additional components can strongly reduce the hematocrit value for the incoming blood 4.

The device 2 is adapted to process the initial liquid medium 4 in vivo and in particular also in vitro. It comprises a separator 6 that is connected to two supply systems 8, 10 and two outlet systems 12, 14.

The separator 6 of the embodiment shown in FIG. 1 is a centrifuge. The separator 6 comprises a separation chamber 16 being rotatable about an axis A of rotation and a drive unit (not shown). The preferred direction of rotation of the separator 6 shown in FIG. 1 is counterclockwise and indicated in FIG. 1 by an arrow R. However, the direction of rotation may also be inverse.

The separation chamber 16 can be a disposable part made from (transparent) plastic material. The separation chamber 16 is designed as an essentially planar spiral channel that winds around the axis A of rotation, with an increasing distance between the channel and the axis A along the direction of rotation R. The separator 6 comprises a volume of 185 ml. Alternatively, other volumes may be used.

The first supply system 8 is adapted to supply the initial liquid medium 4 to be processed (blood) to the separator 6. The first supply system 8 comprises a reservoir 8a that is connected to the innermost end of the spiral channel of the separator 6 (closest to the axis A) via a supply line 8b. The supply line 8b comprises an adjustable pump 8c that is adapted to adjust the flow rate of the initial liquid medium 4 from the reservoir 8a through the supply line 8b to the separator 6.

The first outlet system 12 is adapted to extract the product liquid medium 4' (erythrocyte fraction) from the separator 6 after processing the initial liquid medium 4. The first outlet system 12 comprises a reservoir 12a that is connected to the outermost end of the spiralform channel of the separator 6 (furthest away from the axis A) via an output line 12b. The output line 12b comprises an adjustable pump 12c that is adapted to adjust the flow rate of the product liquid medium 4' from the separator 6 through the output line 12b to the reservoir 12a.

The second supply system 10 is adapted to supply a washing solution 18 to the separator 6. The washing solution 18 can be a physiologic saline solution and is provided to the separator 6 in order to resuspend the cells during processing of the liquid medium 4. In principle the washing solution 18 can be any medium adapted to host cells. For example the medium may be a cell culture medium, plasma, albumin or the like. The second supply system 10 comprises a reservoir 10a that is connected to the separator 6 via a supply line 10b. The supply line 10b reaches the spiral channel of the separator 6 preferably about 90-180° before its outermost end. In general, the position where the supply line 10b reaches the spiral channel is chosen such as to ensure a sufficient separation time for the initial liquid medium 4. Therefore, the supply line 10b should reach the spiral channel not too close to the output line 12b through which the product liquid medium 4' leaves the separator 6 in order to allow the cells to separate or settle down again after the washing step so that the required quality of the product liquid medium 4' can be obtained. Depending on the type of initial liquid medium 4 to be processed and on the type of cells, the position where the supply line 10b reaches the spiral channel can vary. The supply line 10b comprises an adjustable pump 10c that is adapted to adjust the flow rate of the washing solution 18 from the reservoir 10a through the supply line 10b into the separator 6.

The adjustable pumps 8c, 10c and 12c and thus the flow rates of the incoming initial liquid medium 4, the incoming washing solution 18 and the product liquid medium 4' to be extracted can be controlled independently, either manually or by means of a control unit 24 that will be described below.

The second outlet system 14 is adapted to extract waste 20, such as fat, debris, anticoagulants, damaged cells and excess washing solution, from the separator 6 during processing of the initial liquid medium 4. The second outlet system 14 comprises a reservoir 14a that is connected to the separator 6 via an output line 14b. The output line 14b reaches the spiral channel of the separator 6 preferably about 270° after its innermost end. In general, the output line 14b can reach the spiral channel anywhere between the position where the supply line 10b reaches the spiral channel and 360° after the innermost end of the spiral channel. According to FIG. 1, the second outlet system 14 does not comprise an adjustable pump. However, an adjustable pump can be provided that is adapted to adjust the extraction rate of waste 20 from the separator through the output line 14b to the reservoir 14a.

The device 2 further comprises a sensor 22 (e.g. an ultrasonic sensor or an optical sensor) adapted to measure a physical parameter related to the initial concentration of the cells in the initial liquid medium 4 in the first supply system 8. If the initial liquid medium 4 is blood, the sensor 22 might be adapted to measure the hematocrit value of the blood or any related physical parameter (e.g. optical transparency, viscosity, density) from which the hematocrit can be deduced. The hematocrit value of the incoming blood can fluctuate strongly, typically between 5 and 70%. The hematocrit value cup to 85% depending on the time the initial liquid medium 4 stays in the reservoir 8a of the first supply system 8. Preferably, the sensor 22 is provided to measure the hematocrit value of the blood in the supply line 8b between the reservoir 8a and the pump 8c of the first supply system 8 (upstream of the pump 8c). The measurements are performed periodically, e.g. every 5-10 s, the periodicity being adjustable.

Alternatively, the sensor 22 can be provided to measure the hematocrit value of the blood in the reservoir 8a of the first supply system 8 or in the supply line 8b between the pump 8c and the entrance of the separator 6.

The control unit 24 is provided and configured to control at least one process parameter of the device 2 such that the product concentration of the cells in the product liquid medium 4' is within a predefined concentration range that can depend on national standards and customer requirements. The hematocrit of the erythrocyte fraction 4' is preferably between 55 and 70% and more preferably between 60 and 65%.

To this end, the control unit 24 is coupled to the sensor 22 on the one hand and to the respective element of the device related to the process parameter on the other hand (as shown by dashed lines in FIG. 1). In the embodiment in FIG. 1, the respective element is the adjustable pump 10c. The physical parameter related to the concentration of the cells (hematocrit value) measured by the sensor 22 is used as an input signal for the control unit 24 that generates an output signal as a function of the physical parameter measured by the sensor 22. This output signal is used to control the process parameter of the respective element of the device. The control unit 24 is thus adapted to control at least one process parameter of the device 2 as a function of the physical parameter measured by the sensor 22.

According to the embodiment shown in FIG. 1, the process parameter determines the flow rate of the washing solution 18 to the separator 6. The control unit 24 of FIG. 1 is thus coupled to the pump 10c of the second supply system 10 and to the sensor 22.

According to another embodiment (not shown), the control unit 24 can be provided to control several process parameters of the device 2 simultaneously (or another process parameter than the flow rate of the washing solution 18 to the separator 6). In addition (or as an alternative) to the flow rate of the washing solution 18, further process parameters can determine the flow rate of the initial liquid medium 4, the flow rate of the product liquid medium 4' and/or the rotational speed of the separator 6. Correspondingly, the control unit 24 may be coupled to the pump 8c of the first supply system 8, the pump 12c of the first outlet system 12 and/or the drive unit of the separator 6.

In particular, the control unit 24 can be provided to control simultaneously several process parameters determining the flow rate of the washing solution 18, the flow rate of the initial liquid medium 4, the flow rate of the product liquid medium 4' and the rotational speed of the separator 6. In general, the control unit 24 is configured to reduce the flow rate of the washing solution 18, the flow rate of the incoming blood and the rotational speed of the separator 6 and to increase the flow rate of the erythrocyte fraction as the hematocrit value increases. In Table I, an example of the relationship between the hematocrit value and the different process parameters is shown for a device comprising a separator 6 in the form of a rotating separator chamber of the Fresenius Kabi autotransfusion set AT for the continuous autotransfusion system C.A.T.S. described, e.g., by G. Shulman in The Journal Of Extra-Corporeal Technology, Vol, 32, Nr. 1, March 2000, p. 11-19. More specifically, Table I indicates flow ranges and values for the usual operational conditions of the Fresenius Kabi spiral separation chamber. In general, the values will depend on the characteristics of the separator 6 used.

TABLE I

Dependency of the process parameters on the hematocrit value of the incoming blood (revolutions per minute are abbreviated as rpm)

| hematocrit value of the incoming blood (initial liquid medium 4) [%] | rotational speed of the separator [rpm] | flow rate of the washing solution [ml/min] | flow rate of the incoming blood (initial liquid medium 4) [ml/min] | flow rate of the erythrocyte fraction (product liquid medium 4') [ml/min] |
|---|---|---|---|---|
| <15 | >2200 | normal, i.e. >100 | >150 | 5-25 |
| 15-30 | 2100 | normal, i.e. >100 | >100 | 25-100 |
| 30-45 | 1900 | slightly reduced, 85-90% of the normal value | >100 | 100-160 |
| 45-55 | <1900 | Reduced, 55-85% of the normal value | >20 | 160-190 |
| >55 | <1900 | extremely reduced, 30-55% of the | <10 | 160-190 |

TABLE I-continued

Dependency of the process parameters on the hematocrit value
of the incoming blood (revolutions per minute are abbreviated as rpm)

| hematocrit value of the incoming blood (initial liquid medium 4) [%] | rotational speed of the separator [rpm] | flow rate of the washing solution [ml/min] | flow rate of the incoming blood (initial liquid medium 4) [ml/min] | flow rate of the erythrocyte fraction (product liquid medium 4') [ml/min] |
|---|---|---|---|---|
| normal value | | | | |

Alternatively, a centrifuge chamber as described in U.S. 2013/0310241 A1, a disposable centrifuge bowl as described in U.S. Pat. No. 4,943,273, a Latham bowl as described in EP 0 799 645 B1, a C4 dual stage separation chamber as described by T. Zeiler and V. Kretschmer in Infus, Ther. Transfus. Med., Vol 27, Nr. 3, 2000, p. 119-126 and by E. F. Strasser et al. in Transfusion, Vol. 46, January 2006, p. 66-73 or a rotary membrane separation device as described in EP 0 527 973 B1 may be used in the device 2. The concept of variation and process parameter interactions is similar for all these types of separation chambers but the absolute values of the relevant parameters may differ.

Figure 2:
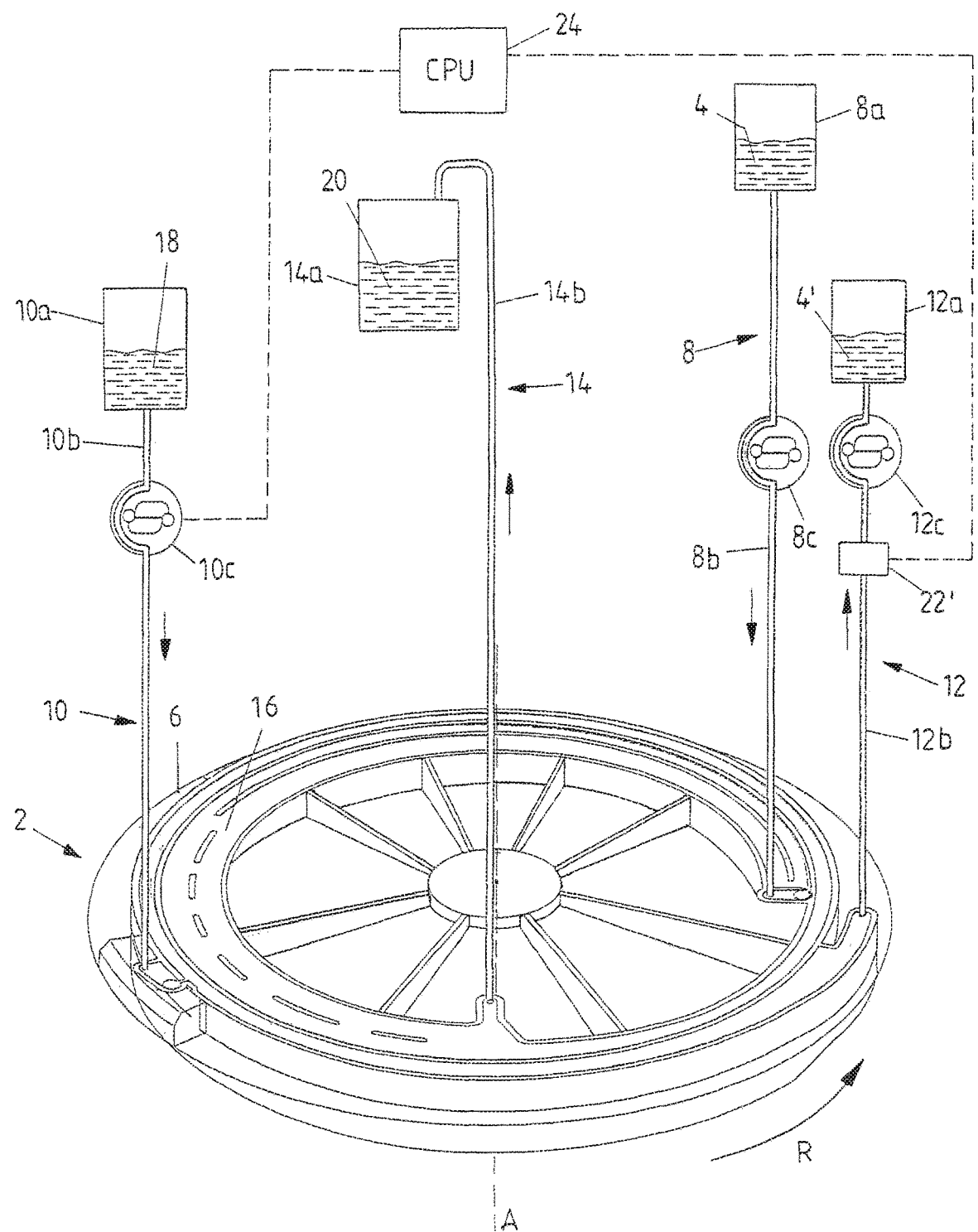
FIG. 2 shows a schematic view of a device for processing a liquid medium comprising cells according to a second embodiment of the invention.

FIG. 2 shows a second embodiment, which differs from the first embodiment essentially by the position of the sensor 22', According to the second embodiment, the sensor 22' is provided between the pump 12c of the first outlet system 12 and the separator 6 (upstream of the pump 12c) and adapted to measure a physical parameter related to the product concentration of the cells in the product liquid medium 4' in the first outlet system 12. Alternatively, the sensor 22' can be provided to measure a physical parameter elated to the product concentration of the cells in the product liquid medium in the reservoir 12a of the first outlet system 12 or in the output line 12b between the pump 12c and the reservoir 12a. If the product liquid medium 4' is formed by the erythrocyte fraction of the blood fed into the separator 6, then the sensor 22' (e.g. an ultrasonic sensor or an optical sensor) may be adapted to measure the hematocrit value or a physical parameter related to the hematocrit value of the erythrocyte fraction. In this case, the sensor 22' has to be adapted to measure an elevated hematocrit value (between 50 and 90%) of the erythrocyte fraction. The measurements are performed periodically, e.g. every 5-10 s, the periodicity being adjustable.

Further, the sensor 22' measuring the hematocrit value of the erythrocyte fraction can serve for quality management. To this end, the hematocrit value can be measured throughout the entire blood processing treatment. Integration of the hematocrit value over time (in particular the time interval of the entire blood processing treatment) leads then to the total red cell content of the entire erythrocyte fraction in the reservoir 12a of the first outlet system 12. The total red cell content divided by the volume measured by the pump 12c results in the total average hematocrit of the erythrocyte product in the reservoir 12a.

Also the sensor 22 of the first embodiment measuring the hematocrit value of the blood to be processed can serve for determining the total red cell content of the blood to be processed.

The physical parameter related to the initial or product concentration of the cells can be graphically illustrated as a function of time in order to simplify the analysis of the processing treatment, the composition of the initial liquid medium 4 and the composition of the product liquid medium 4'.

Figure 3:
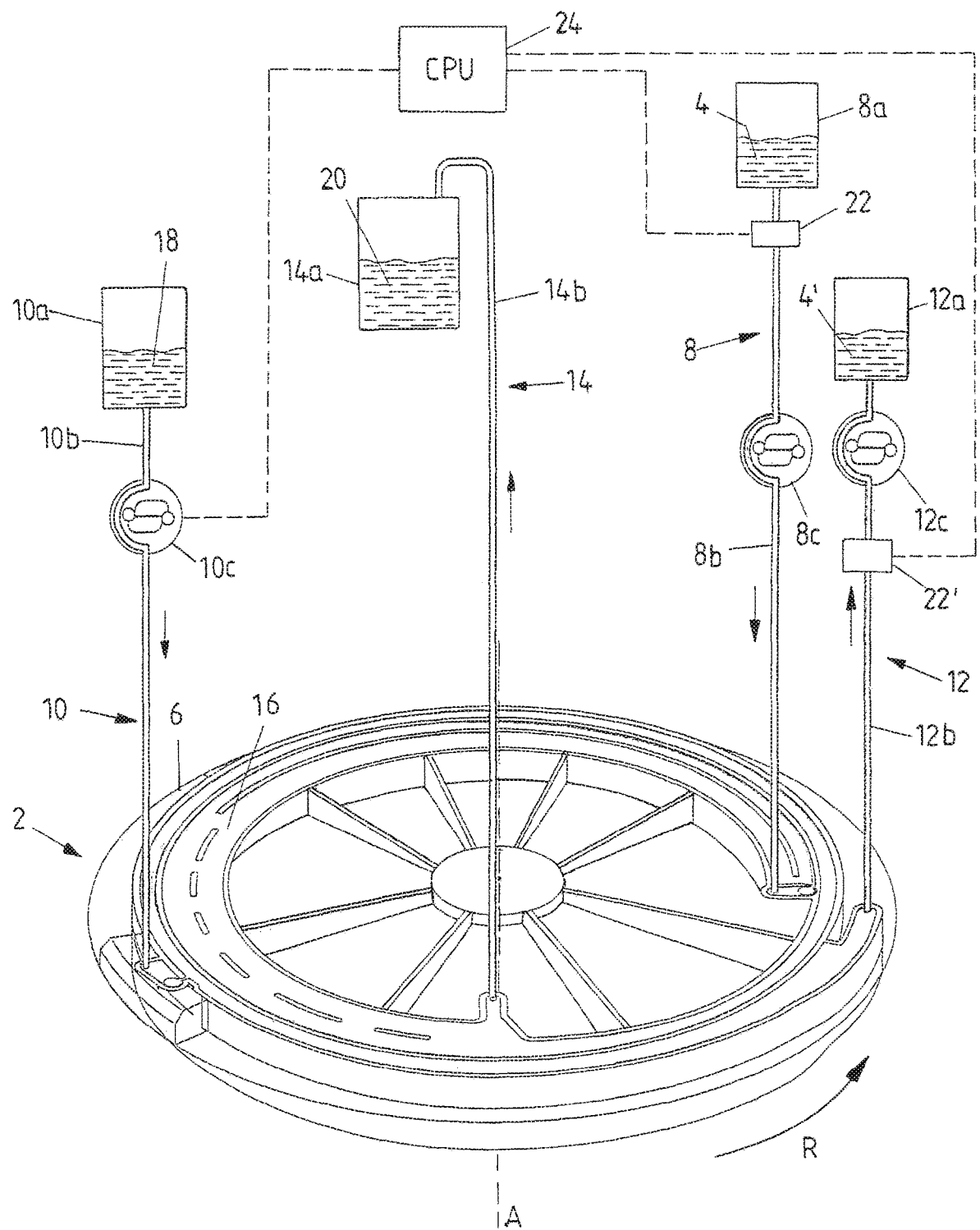
FIG. 3 shows a schematic view of a device for processing a liquid medium comprising cells according to a third embodiment of the invention.

According to a third embodiment shown in FIG. 3, the device 2 comprises two sensors 22, 22'. The first sensor 22 is adapted to measure a physical parameter related to the initial concentration of the cells in the initial liquid medium 4 in the first supply system 8. The second sensor 22' is adapted to measure a physical parameter related to the product concentration of the cells in the product liquid medium 4' in the first outlet system 12. Preferably the sensors 22, 22' are provided in the first supply system 8 and in the first outlet system 12 upstream of the corresponding pumps 8c, 12c, respectively. Alternatively, the sensors 22, 22' can be provided anywhere else in the first supply system 8 and the first outlet system 12, respectively.

Both sensors 22, 22' are coupled to the control unit 24 as shown by dashed lines in FIG. 3 and the physical parameters measured by the sensors 22, 22' are used as input signals for the control unit 24 that generates an output signal as a function of the physical parameters measured by the sensors 22 and 22'. The first sensor 22 monitors the hematocrit value of the initial liquid medium 4 in analogy to the sensor 22 in the first embodiment (FIG. 1). The second sensor 22' monitors the hematocrit value of the product liquid medium 4' and thus the effect of the control that is based on the measurements of the first sensor 22. The second sensor 22' may provide an instantaneous feedback to the control unit 24 in order to further modify the process parameters of the device 2 if necessary.

The use of said two sensors 22, 22' allows to determine the total red cell content of the blood to be processed and the total red cell content of the entire erythrocyte fraction in the reservoir 12a of the first outlet system 12, as already outlined for the first and second embodiment. The use of said two sensors 22, 22' further allows to calculate the yield (also known as efficiency, yield rate, collection rate, recovery, recovery rate or effectiveness) of cells after processing the initial liquid medium in the device 2 on the basis of the following equation:

$$\text{yield } [\%] = \frac{V_{product\ liquid\ medium} \cdot \text{product concentration} \cdot 100}{V_{initial\ liquid\ medium} \cdot \text{initial concentration}}.$$

The control unit 24 of the third embodiment is configured to control the flow rate of the washing solution 18 to the separator 6 and is thus coupled to the pump 10c of the second supply system 10, as shown in FIG. 3.

In analogy to the embodiments shown in FIGS. 1 and 2, the control unit 24 can also be configured to control several process parameters of the device 2 simultaneously (or another process parameter than the flow rate of the washing solution 18 to the separator 6). In addition (or as an alternative) to the flow rate of the washing solution 18, the process parameters can determine the flow rate of the initial liquid medium 4, the flow rate of the product liquid medium 4' and/or the rotational speed of the separator (centrifuge) 6. Correspondingly, the control unit 24 may also be coupled to the pump 8*c* of the first supply system 8, the pump 12*c* of the first outlet system 12 and/or the drive unit of the separator 6.

In particular, the control unit 24 can be provided to control simultaneously several process parameters determining the flow rate of the washing solution 18, the flow rate of the initial liquid medium 4, the flow rate of the product liquid medium 4' and the rotational speed of the separator 6.

In case of a defect of one of the two sensors 22, 22', the device 2 is able to continue operation with the remaining sensor.

For in vitro processing of an initial liquid medium 4 comprising cells in an initial concentration in order to obtain a product liquid medium 4' comprising cells in a product concentration, the device 2 can be used to obtain a product liquid medium 4' with a predetermined product concentration of cells or with a maximum product concentration of cells. Below, the method shall be described using blood as an initial liquid medium 4 that shall be processed to obtain the erythrocyte fraction of the blood as a product liquid medium 4'.

First, the reservoir 8*a* of the first supply system is (partially) filled with a predetermined amount (e.g. more than 100 ml) of blood and the reservoir 10*a* of the second supply system is filled with a washing solution 18, such as a physiologic saline solution, a cell culture medium, plasma, albumin or the like, for washing purposes during processing. The blood is transferred with a defined flow rate from the reservoir 8*a* into the separator 6 via the pump 8*c* of the first supply system 8. Before passing said pump 8*c*, the hematocrit of the blood or a physical parameter related to the hematocrit allowing for its calculation is measured by a sensor 22. The value measured by the sensor 22 is transmitted to the control unit 24 and is used to determine a control signal as a function of the measured value according to the relationship shown in Table I. The control signal is used to control one or more process parameters that may be chosen from the flow rate of the washing solution 18, the flow rate of the initial liquid medium 4, the flow rate of the product liquid medium 4' and/or the rotational speed of the separator 6. In particular, the control unit 24 reduces the flow rate of the washing solution 18, the flow rate of the incoming blood and the rotational speed of the separator 6 and increases the flow rate of the erythrocyte fraction as the hematocrit value increases.

In the separation chamber 16 of the separator 6, the blood is subject to a first separation phase. The rotational speed of the separator 6 depends on the hematocrit determined for the incoming blood by sensor 22. In this phase, the blood is enriched to a hematocrit of approximately 80%. Plasma, fat, debris, anticoagulants or damaged cells are washed out via the second outlet system 14 and are collected in the reservoir 14*a* of the second outlet system 14.

In a subsequent washing phase, the washing solution 18 is added to the separation chamber 16 in order to resuspend the erythrocytes that are present in the enriched blood.

Residual plasma, fat, debris, anticoagulants or damaged cells are washed out via the second outlet system 14.

After the washing phase, the partially processed blood is subject to a second separation phase during which the washing solution 18 is washed out by centrifugation. The erythrocytes are packed to a hematocrit of 60 to 6% and the erythrocyte fraction is separated out via the first outlet system 12 and is collected in the reservoir 12*a* of the first outlet system 12.

Optionally, the hematocrit of the erythrocyte fraction can be determined by a second sensor 22' located between the separator 6 and the reservoir 12*a*. The hematocrit value of the erythrocyte fraction can serve for information purposes. Additionally, the hematocrit of the erythrocyte fraction (or a physical parameter related to the hematocrit) can be used to control one or more process parameters of the device by means of the control unit 24.

Although the device and method for processing an initial liquid medium comprising cells in an initial concentration in order to obtain a product liquid medium comprising cells in a product concentration have been exemplarily described for blood as the initial liquid medium and its erythrocyte fraction as the product liquid medium, said device and method are not limited to these substances. They can also be employed to separate stem cells from a nutrient solution, or to separate other cellular blood constituents than erythrocytes from blood, or to separate different cell types from one another,

The invention claimed is:

1. A method for processing an initial liquid medium composing cells in an initial concentration in order to obtain a product liquid medium comprising cells in a product concentration, the method comprising the following steps:
    supplying the initial liquid medium to a separator via a first supply system,
    in the separator, separating the initial liquid medium into various constituents including the product liquid medium,
    extracting the product liquid medium from the separator via a first outlet system,
    measuring a physical parameter related to the concentration of the cells in the initial liquid medium using a sensor, and
    controlling at least one process parameter as a function of the physical parameter measured by the sensor,
    wherein, during the step of separating the initial liquid medium into various constituents, a solution is supplied to the separator at a flow rate via a second supply system,
    the flow rate of the solution in the second supply system during its supply to the separator being determined based on the at least one process parameter, and the flow rate of the solution in the second supply system being reduced when the concentration of the cells measured in the initial liquid medium increases.

2. The method according to claim 1, wherein the initial liquid medium is supplied at a flow rate in the first supply system to the separator determined based on the at least one process parameter.

3. The method according to claim 2, wherein the flow rate of the initial liquid medium is indirectly proportional to the initial concentration of the cells in the initial liquid medium in the first supply system.

4. The method according to claim 2, wherein the product liquid medium is extracted at a flow rate in the first outlet system from the separator determined based on the at least one process parameter.

5. The method according to claim 4, wherein the flow rate of the product liquid medium is directly proportional to the initial concentration of the cells in the initial liquid medium in the first supply system.

6. The method according to claim 1, wherein the product liquid medium is extracted at a flow rate in the first outlet system from the separator determined based on the at least one process parameter.

7. The method according to claim 6, wherein the flow rate of the product liquid medium is directly proportional to the initial concentration of the cells in the initial liquid medium in the first supply system.

8. The method according to claim 1, wherein the step of separating the initial liquid medium into various constituents comprises centrifuging the initial liquid medium.

9. The method according to claim 8, wherein the initial liquid medium is centrifuged at a rotational speed determined based on the at least one process parameter such that the rotational speed is indirectly proportional to the initial concentration of the cells in the initial liquid medium in the first supply system.

10. The method according to claim 1, wherein, during the step of controlling the at least one process parameter, the product concentration of the cells in the product liquid medium is within a predefined concentration range.

11. The method according to claim 1, further comprising measuring a physical parameter elated to the product concentration of the cells in the product liquid medium using another sensor.

12. The method according to claim 1, wherein the liquid medium is blood comprising blood cells.

* * * * *